United States Patent [19]

Sommer et al.

[11] Patent Number: 4,473,639

[45] Date of Patent: Sep. 25, 1984

[54] REAGENT STRIP TEST FOR ANTITHROMBIN-III

[75] Inventors: Ronald G. Sommer; Alfred C. Greenquist, both of Elkhart, Ind.

[73] Assignee: Miles Laboratories, Inc., Elkhart, Ind.

[21] Appl. No.: 418,285

[22] Filed: Sep. 15, 1982

[51] Int. Cl.³ .................. C12Q 1/56; C12Q 1/38; C12N 9/96; C12N 9/99
[52] U.S. Cl. .................................. 435/13; 435/23; 435/184; 435/188; 435/805
[58] Field of Search ............... 435/4, 7, 13, 23, 24, 435/214, 184, 188, 805, 810; 422/56, 57

[56] References Cited

U.S. PATENT DOCUMENTS

| | | | |
|---|---|---|---|
| 4,061,625 | 12/1977 | Ekenstam et al. | 435/13 |
| 4,221,706 | 9/1980 | Ali et al. | 435/13 |
| 4,234,682 | 11/1980 | Bartl et al. | 435/13 |
| 4,275,153 | 6/1981 | Gargiulo et al. | 435/13 |
| 4,324,858 | 4/1982 | Goodson et al. | 435/805 |
| 4,363,874 | 12/1982 | Greenquist | 435/7 |
| 4,390,343 | 6/1983 | Walter et al. | 435/805 |

OTHER PUBLICATIONS

Odegard, et al., *Thrombosis Research*, vol. 6, pp. 287–294, (1975).

*Primary Examiner*—Esther M. Kepplinger
*Attorney, Agent, or Firm*—Jerome L. Jeffers

[57] ABSTRACT

Disclosed is a method and device for the quantitative determination of AT-III in mammalian blood plasma. The method involves contacting a plasma sample containing excess heparin with a 3 layered reagent strip comprising:

i. a first upper layer of a bibulous material containing thrombin and a buffer;
ii. a second lower layer of a bibulous material containing a fluorogenic or chromogenic substrate capable of interacting with thrombin in a time related chemical manner; and
iii. a bottom layer of water impermeable material.

The chemical change in the strip is determined as a function of time and this change is compared with that obtained in samples containing known amounts of AT-III.

10 Claims, 7 Drawing Figures

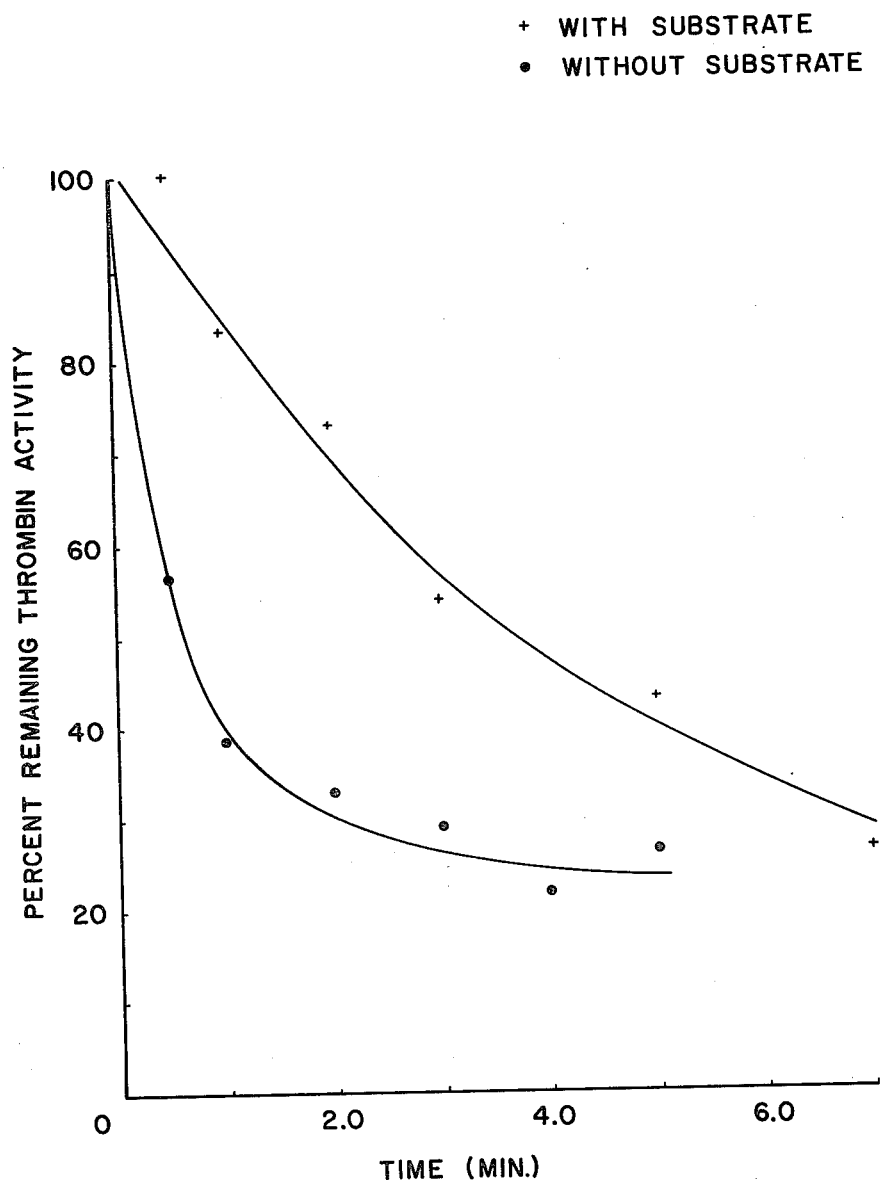
INHIBITION OF THROMBIN IN SOLUTION BY PLASMA AT-III IN THE PRESENCE AND IN THE ABSENCE OF S-2238 SUBSTRATE
FIG. I

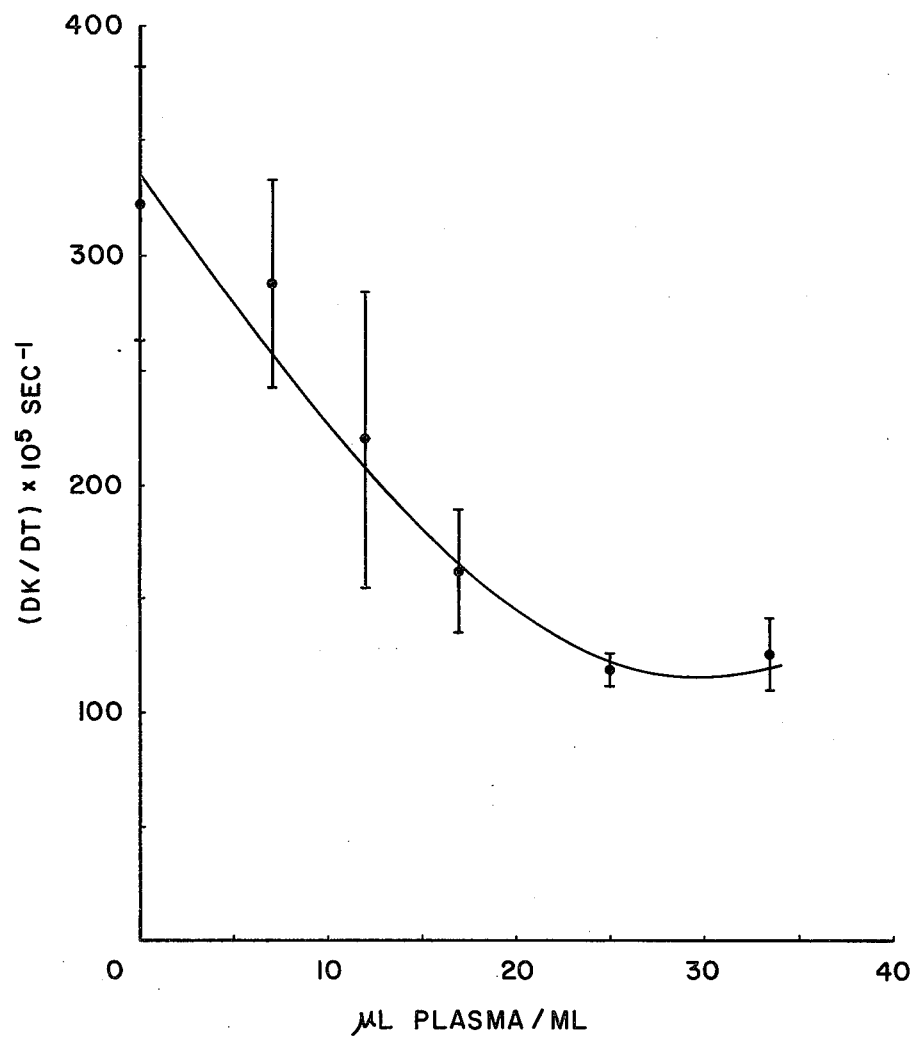
THE RESPONSE OF CHROMOGENIC DOUBLE-LAYERED STRIP
PREPARATION I TO PLASMA AT -III DILUTED IN AQUEOUS HEPARIN
FIG. II

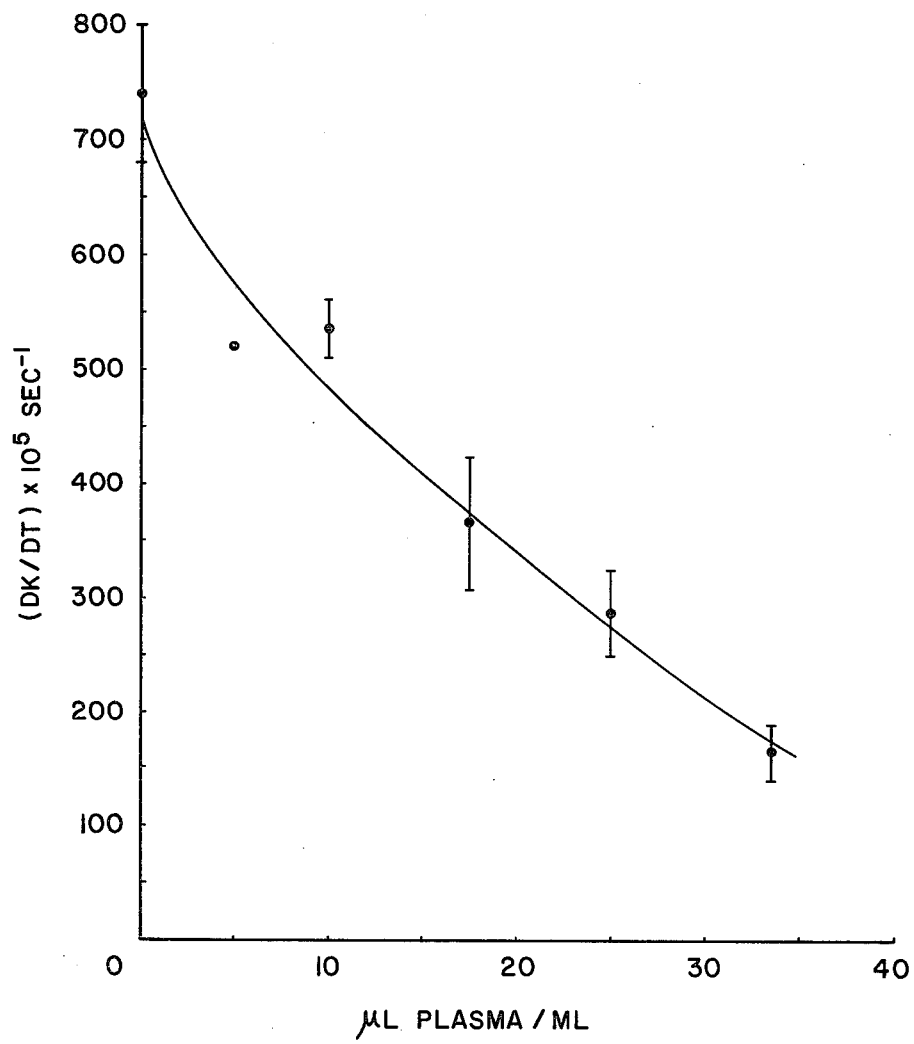
THE RESPONSE OF CHROMOGENIC DOUBLE-LAYERED STRIP
PREPARATION II TO PLASMA AT-III DILUTED IN AQUEOUS HEPARIN
FIG. III

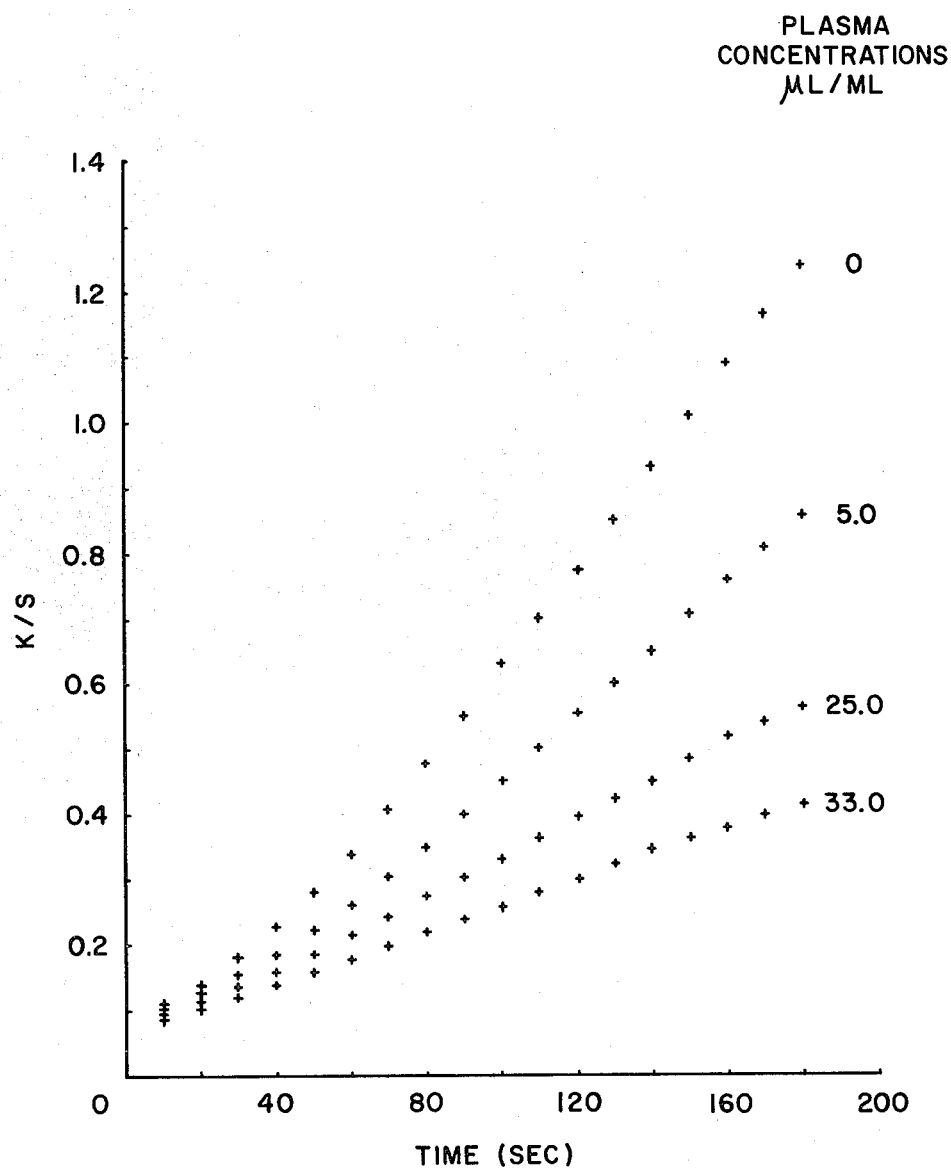
K/S VS TIME PLOTS FOR CHOSEN PLASMA
AT-III CONCENTRATIONS ADDED IN AQUEOUS
HEPARIN TO CHROMOGENIC STRIP PREPARATION II
FIG. IV

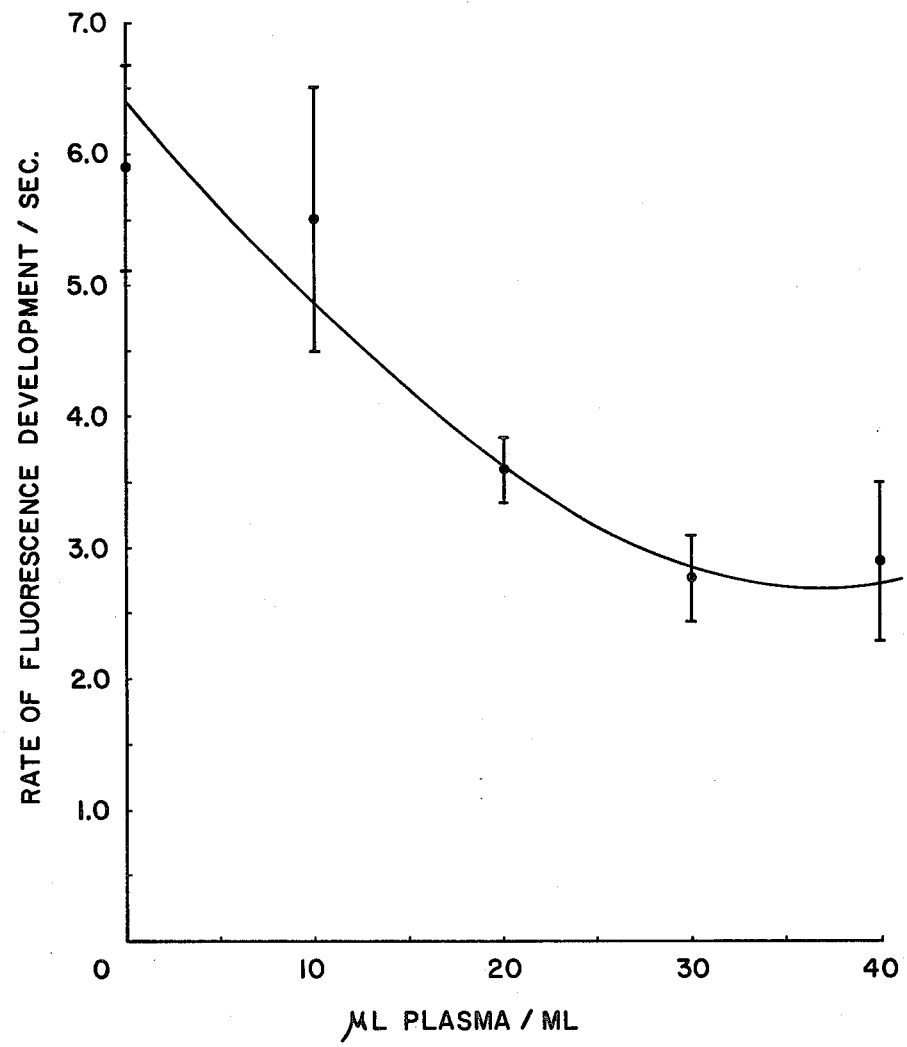
THE RESPONSE OF THE FLUOROGENIC DOUBLE-LAYERED STRIP TO PLASMA AT-III DILUTED IN AQUEOUS HEPARIN
FIG. V

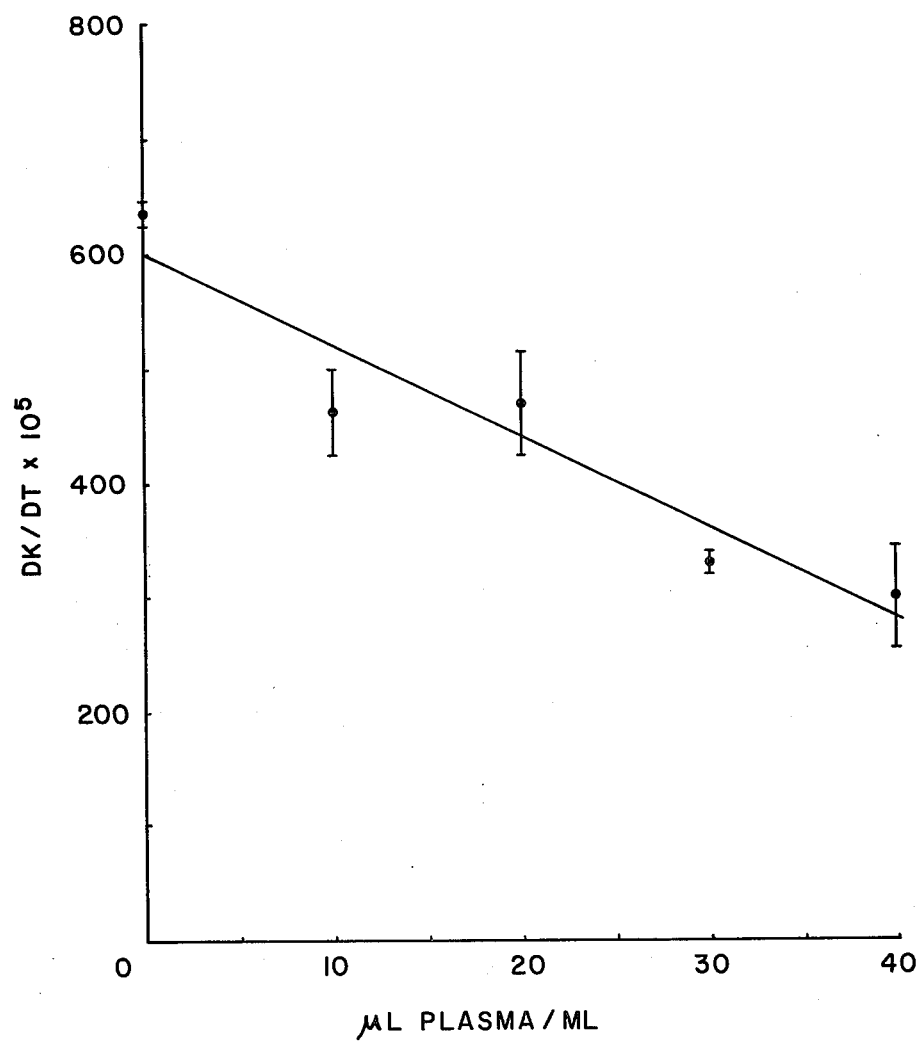
THE RESPONSE OF DOUBLE - LAYERED CHROMOGENIC STRIP PREPARATION III TO AQUEOUS DILUTIONS OF PLASMA AT - III
FIG. VI

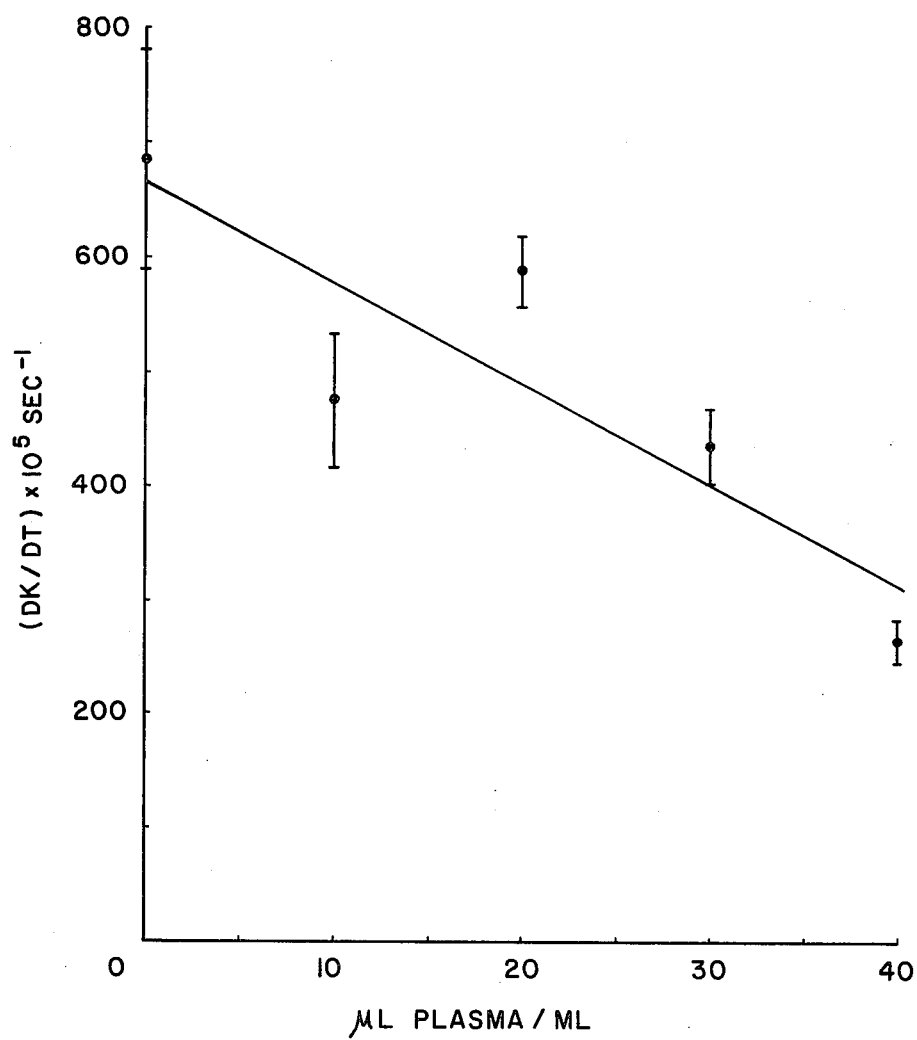
THE RESPONSE OF DOUBLE-LAYERED CHROMOGENIC STRIP
PREPARATION IV TO AQUEOUS DILUTIONS OF PLASMA AT-III
FIG. VII

REAGENT STRIP TEST FOR ANTITHROMBIN-III

BACKGROUND OF THE INVENTION

In recent years, a large volume of literature has evolved concerning the use of small peptide substrates for the assay of specific proteinases. These substrates usually contain a chromogenic or fluorogenic group which is released upon hydrolysis by the proteinase whereupon the rate of appearance of color or fluorescence can be used to quantify the amount of proteinase enzyme present. This development has made it possible to assay individually many of the serine proteinases involved in the blood coagulation cascade. Peptide substrates specific for thrombin and factor Xa have been used to develop indirect solution assays for the clinically important blood coagulation inhibitor antithrombin-III (AT-III), which is thought to be the major inhibitor of thrombin and factor Xa in plasma. These assays rely on the fact that AT-III is a rapid inhibitor of thrombin in the presence of heparin. The inhibition takes from 10 to 60 minutes in the absence of heparin but only 15 to 60 seconds in its presence. The reaction sequence in these assays is represented by the following equations:

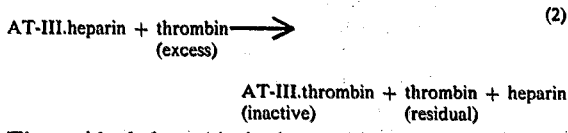

The residual thrombin is then assayed using a suitable synthetic peptide substrate. For the assay of AT-III, heparin is provided in excess of the catalytic amount required so that all of the AT-III present in the assay can rapidly exert its thrombin inhibiting effect. To determine the amount of heparin necessary, a titration experiment with increasing amounts of heparin could be run to determine the amount necessary to give the desired result. In the experiments described herein, this assay was not performed, but instead the amounts of heparin used in similar samples diluted for a solution assay were used. It is reported by Blombock, et al [Throm. Diath. Haemouh. 9, 368 (1963)] that the inhibition of thrombin was constant between 2 and 16 U/ml of heparin. In all of the published assays for AT-III there is a time delay after reaction (2) which preceeds the addition of a synthetic peptide substrate to assay the residual thrombin. It has been discovered that this delay is necessary because the heparin catalyzed reaction of AT-III and thrombin proceeds very slowly in the presence of substrates which have low Km values. In many of the assays, an additional constituent, polybrene, is added along with the peptide substrate to neutralize the heparin and prevent any further fast inhibition of thrombin during the assay of residual thrombin. The use of polybrene or another heparin neutralizing substance was initially tried with assays that employ chromogenic thrombin substrates having rather high Km values. This was necessary because the substrate does not compete well with any unreacted AT-III.heparin complex and further inhibition could occur during the hydrolysis step. This practice was carried over into some assays in which chromogenic substrates having lower Km values were employed. The substrate used in the work reported in the following examples, S-2238, has a very low Km value and it was found that polybrene was not necessary.

An assay of the type above is described by Odegard, et al in *Thrombosis Research*, Vol. 6, pages 287-294 (1975) Pergamon Press, Inc. This assay involves mixing 100 microliters ($\mu$l) of test plasma with 2.9 milliliters (ml) of buffer containing heparin whereupon 400 $\mu$l of this dilution is trasferred into each of 2 glass tubes and prewarmed in a water bath at 37° C. for 2 to 6 minutes. At this point, 100 $\mu$l of a thrombin solution containing 30 NIHU/ml is blown into the tube, and after exactly 30 seconds, 300 $\mu$l of a substrate-polybrene solution is blown into the reaction mixture. The chromogenic substrate used is the tripeptide Bz-Phe-Val-Arg-pNA.HCl. Exactly 60 seconds after addition of the substrate, the amidolysis is quenched by blowing 300 $\mu$l of acetic acid into the mixture. The optical density is read at 405 nanometers (nm) against a reagent blank containing 400 $\mu$l standard plasma dilution, 300 $\mu$l acetic acid, 300 $\mu$l substrate-polybrene solution and 100 $\mu$l thrombin solution mixed in this order. Two optical density readings are taken and their mean is used for reading the AT-III concentation (heparin cofactor activity) from a standard curve.

While this wet assay method is more convenient than earlier assays which involve clotting of fibrin, it is still somewhat time consuming and can be susceptible to human error. A test strip for the quantitative determination of AT-III based on the interaction of thrombin and a chromogenic or fluorogenic substrate would be desirable. However, any increase in speed or convenience obtained by employing a strip containing thrombin and the substrate in close proximity to each other would be more than offset by the fact that the presence of the substrate inhibits the reaction between thrombin and AT-III even in the presence of excess heparin.

SUMMARY OF THE INVENTION

The present invention is a method for the quantitative determination of AT-III in mammalian blood plasma. The method comprises:
(a) contacting the plasma with excess heparin and a 3 layered reagent strip comprising:
  i. a first upper layer of a carrier matrix having absorbed therein thrombin and a buffer;
  ii. a second lower layer adjacent to and in liquid communication with the first layer said second layer comprising a carrier matrix having absorbed therein a thrombin sensitive fluorogenic or chromogenic substrate and a buffer, said substrate being capable of interacting with thrombin in such a manner that a time related chemical change detectable by spectrofluorometric or spectrophotometric means takes place when thrombin and the substrate are contacted in a suitable liquid environment; and
  iii. a layer of water impermeable material beneath the lower layer;
(b) monitoring any chemical change in the substrate by reflectance spectrofluorometric or spectrophotometric means repeatedly over a period of time to obtain at least 2 reflectance spectrofluorometric or spectrophotometric values as a function of time; and
(c) comparing the relationship between the values obtained in step (b) with values obtained in a like manner using plasma samples containing known amounts of AT-III and using such comparison to determine the concentration of AT-III in the plasma sample being tested.

DETAILED DESCRIPTION

The adaptation of the solution technology for the assay of AT-III and heparin using synthetic fluorogenic or chromogenic substrates to paper reagent strips is complicated by the necessity for timed sequential addition of reagents. By constructing a double layered reagent strip with the bottom pad containing substrate and the top pad containing thrombin and optionally heparin, and applying the plasma sample to the top layer, the plasma AT-III has enough time after contacting the thrombin in the top pad to form the AT-III thrombin complex before diffusion of the substrate from the lower pad becomes significant enough to cause inhibition. There should be a water impermeable material beneath the lower pad so that sample solution does not flow on to the table of the measuring instrument and to ensure that diffusion of the substrate into the top pad will take place.

The first top layer of the test strip comprises a carrier matrix having thrombin absorbed therein. The carrier material should be a substance which is capable of absorbing the blood plasma while allowing a portion of it to flow through into the bottom pad. The bottom pad, which may be of the same material, has the substrate absorbed therein, and functions by allowing the plasma fluid to solubilize the substrate and permitting it to diffuse from the bottom pad to the upper pad after the thrombin-AT-III complex has formed. It has been discovered that materials commonly used in the fabrication of diagnostic test strips are suitable for this purpose. Suitable materials which can be used include films formed of gelatin or agarose. Typically, a bibulous material such as, for example, paper, cellulose, wood, synthetic resin fleeces, woven and nonwoven fabrics and the like is used to form the carrier matrix.

The carrier matrix can be soaked, immersed in, sprayed or printed with the liquid reagent composition and dried by suitable means, such as ambient or forced air drying to leave the dry reagent/matrix combination. When the carrier is a bibulous material this will leave the reagent absorbed in the carrier matrix. The top layer is prepared by contacting the carrier matrix with a solution of thrombin and a buffer. The buffer is necessary because the rate of the thrombin enzamatic reaction is pH dependent. The pH of the buffer in both pads of the strip is designed at maximizing the reaction of thrombin with the substrate. When the substrate is S-2238, the maximum esterolytic response of thrombin is achieved at pH 8.0 to 8.5. Suitable buffers include, for example, tris(hydroxymethyl)-aminomethane (TRIS); N,N-bis-(2-hydroxymethyl) glycino and tris(hydroxymethyl)methylaminopropanesulfonic acid. In addition, the solution should contain a material which will stabilize the thrombin during the drying step, such as BSA (bovine serum albuim). A typical solution will contain thrombin in a concentration of from 2 to 5 NIH units/ml and contain 0.2% (w/v) BSA to stabilize the thrombin during drying of the paper.

The bottom layer is prepared from a solution typically containing about 5 mM substrate in water solution. A buffer the same or different than that used in the top layer is used in this dip solution.

Suitable chromogenic and fluorogenic substrates, their tradenames where applicable, formula and detection method are set out in Table I.

TABLE I

| Trade Name/Source | Formula* | Detection Method |
| --- | --- | --- |
| S-2160 A.B. KABi | Bz—phe—ala—arg—pNA | Absorbance at 405 nm |
| S-2238 A.B. KABi | H—D-phe—pip—arg—pNA | Absorbance at 405 nm |
| Chromozym ® TH Pentapharm LTD | Tos—gly—pro—arg—pNA | Absorbance at 405 nm |
| Abbott Qualtichrome Abbott Laboratories | CH$_3$—gly—pro—arg—pNA | Absorbance at 405 nm |
| No trade name Enzyme Systems Products | CBZ—gly—pro—arg—4MNA | Fluorescence & Absorbance Excitation-360 nm; Emission 420 nm. Absorbance at 525 nm after coupling with Fast Blue B |
| No trade name Enzyme Systems Products | H—D-phe—pro—arg—AIE | Fluorescence Excitation-335 nm; Emission-438 nm |
| No trade name Enzyme Systems Products | H—D-phe—pro—arg—4MNA | Fluorescence & Absorbance Excitation-360 nm; Emission-420 nm. Absorbance at 525 nm after coupling with Fast Blue B |
| No trade name Enzyme Systems Products | H—D-phe—pro—arg—AFC | Fluorescence & Absorbance Excitation-400 nm; Emission-505 nm Absorbance at 380 nm |
| No trade name Peptide Institute, Japan | BOC—Val—pro—arg—MCA | Fluorescence Excitation-380 nm; Emission-460 nm |

*The abbreviated chromophores & fluorophores are as follows:
pNA - p-nitroaniline
4MNA - 4-methoxy-β-naphthylamine
AIE - 5-aminoisophthalic acid dimethylester
AFC - 4-trifluoromethyl-coumaryl-7-amine
MCA - 4-methyl-coumaryl-7-amine The present invention is further illustrated by the following examples. In these examples, TRIS, BSA and thrombin (bovine thrombin) were obtained from the Research Products Division of Miles Laboratories, Inc. Whatman 54 paper was from the Whatman Paper Company, the plasma was Thromboscreen® Universal Coagulation Reference Plasma from Cutter Laboratories, Inc. and S-2238 substrate was from A.B. KABI. Substrates H-D-phe-pro-arg-AIE and H-D-hpe-pro-arg-AFC were from Enzyme Systems Products and heparin was sodium heparin (porcine intestinal mucosa) from Sigma.

In these examples reflectance or fluorescence measurements were taken at the optimum wavelength for each indicator after applying a plasma dilution to the strips. The percent reflectance values were converted into K/S values by using the following formula:

$$K/S = [(1-R)^2/2R]$$

where K is the absorption coefficient of the sample, S is the light scattering coefficient of the matrix and R is the fraction of incident light reflected from the reagent pad. This is a simplified version of the Kubelka-Munk equation. The K/S values are related to reflectance measurements.

Preparation of Reagent Containing Paper

Method A

Three inch square pieces of Whatman 54 paper from the Whatman Paper Company were saturated with at least 0.1 ml of dip solution, pulled through scraper bars, mounted on either a piece of cardboard with a 2¾ inch by 2¾ inch hole cut in it or mounted on nylon mesh. The mounted pieces of paper were suspended in a forced air drying oven and dried for the appropriate length of time.

Method B

A 3 by 9¾ inch piece of Whatman 54 paper was dipped into 10 ml of solution, pulled through scraper bars, suspended on a rack in a forced air drying oven and dried for the appropriate amount of time.

Method C

A 4 inch wide Whatman 54 paper strip was run on an automated dipping apparatus using 100 ml of dip solution using a paper speed of 31.4 inches/minute, a drying temperature of 50° C. in the 3 dryer sections and an air flow rate of 1, 1.5 and 1.5 inches in dryer sections 1, 2 and 3, respectively.

Preparation of Reagent Strips

Method 1

The dried reagent paper was mounted on a reflective mylar foil with double sided adhesive, the edges trimmed and the laminate slit into 1 cm wide strips. These strips were mounted ¼ inch from the front of white tricite plastic handle material via the double sided adhesive and the resulting laminates slit into either 5 mm wide strips for chromogenic work or 10 mm wide strips for fluorogenic work. All strips were stored at 4° C. with 3 to 4 molecular sieve tables per storage bottle.

Method 2

The steps in Method 1 were performed, but before final slitting, a second pad was placed over the top of the first pad as follows:
(a) The reagent paper for the top pad was trimmed and slit into 1 cm wide strips.
(b) A 1-2 mm wide strip of double sided adhesive was cut and placed at the back edge of the bottom reagent pad which was already mounted on tricite.
(c) A 1 cm wide strip of reagent paper for the top pad was bound to the lower pad via the strip of double sided adhesive.
(d) The resulting laminate was slit into either 5 mm or 10 mm wide reagent strips.

Method 3

The steps of method 1 were performed, but before final slitting, polypropylene mesh and a second reagent pad were placed over the top of the first pad as follows:
(a) The reagent paper for the top pad was trimmed and slit into 1 cm wide strips and 149 micron polypropylene mesh was cut by hand into 1 cm wide strips.
(b) 1-2 mm wide strips of double sided adhesive were cut and placed at both the front and back edges of the bottom reagent pad which was already mounted on tricite.
(c) A 1 cm wide piece of 149 micron polypropylene mesh was bound to the lower pad via the double sided adhesive strips.
(d) A 1-2 mm wide strip of double sided adhesive was cut and placed at the back edge of the propylene mesh.
(e) A 1 cm wide strip of reagent paper for the top pad was bound to the lower pad via the strip of double sided adhesive on the mesh.

EXAMPLE I

Examination of the Inhibition of Thrombin by AT-III

The method of Odegard, et al previously described, was used to examine the inhibition of thrombin at AT-III in solution. It was theorized that the inhibition would proceed fairly rapidly even in the presence of substrate and that, therefore, the reduction of this technology to strip chemistry would be facilitated. The percent remaining thrombin activity was determined when thrombin and AT-III were incubated together in the absence of the S-2238 substrate by a modification of the method of Odegard, et al. The procedure was as follows:

(a) A 150 fold dilution of Thromboscreen Universal Reference Plasma was made in 0.05M TRIS, 0.19M NaCl, 3 USP $\mu m/ml$ heparin, pH 9.1.
(b) Four hundred (400) microliters of the dilution in (a) was placed in a test tube and equilibrated at 37° C.
(c) One hundred (100) microliters of a 2.0 NIH unit/ml bovine thrombin solution was added and mixed. The National Institute of Health performs a service by dispensing standard thrombin samples. These samples contain a specified number of enzymatic units. Thus, the term NIH unit is derived from a comparison to these standard materials.
(d) After the desired incubation time, 300 $\mu l$ of 0.26 mg/ml water solution of S-2238 substrate (previously warmed to 37° C.) was added.
(e) After a 2 minute incubation at 37° C., 300 $\mu l$ of glacial acetic acid was added to stop the reaction and the absorbance at 405 nm was measured.
(f) The absorbance for a reaction containing no plasma was taken as 100 percent remaining thrombin activity.

Since a similar method could not be used to examine the inhibition of thrombin by AT-III in the presence of S-2238 substrate, the following method was used:
(a) A mixture of 2.98 ml of 0.05M TRIS, 0.19M NaCl, 3 USP units/ml heparin, pH 9.1 buffer+2.25 ml of a 0.26 mg/ml water solution of S-2238 substrate+20 µl thromboscreen was prepared.

(b) The solution described in (a) was incubated at 37° C. for 15 minutes and then 750 µl of a 2.0 NIH unit/ml solution of bovine thrombin was added and mixed. The time of addition was taken as time=0.

(c) At specified intervals, 800 µl aliquots of this solution were removed and mixed with 300 µl of glacial acetic acid to stop the reaction.

(d) The absorbance at 405 nm was measured.

(e) The rate was calculated assuming the regression line of 3 adjacent points would have a similar slope to the tangent to the curve at the middle point of the 3 points.

(f) The rate in the absence of plasma was taken as 100 percent remaining thrombin activity.

The plot of the data so generated is set out in FIG. I. From FIG. I it can be determined that, although the inhibition of thrombin by AT-III is very rapid in the absence of S-2238, in the presence of this substrate the inhibition is much slower and does not proceed to completion for 7 or 8 minutes.

In agreement with this, it was found that when plasma AT-III was diluted 60 fold into aqueous heparin containing 2 mM S-2238 substrate and 30 µl was applied to thrombin containing reagent strips, only an insignificant amount of inhibition was seen in the 5 minutes for which the strip reflectance was observed. However, a response to plasma AT-III concentration was observed when 15 µl of various dilutions of Thromboscreen Universal Reference Plasma in aqueous heparin was applied to the same strips, the strip incubated 1 minute with this solution and then 15 µl of 4 mM S-2238 substrate added and the reflectance followed.

EXAMPLE II

A Chromogenic Strip Responsive to Plasma AT-III Diluted In Aqueous Heparin

Based on the results of Example I, it was hypothesized that a double layered strip containing substrate in the bottom pad and thrombin in the top pad should be considered because when samples containing plasma AT-III diluted into aqueous heparin were applied to such a strip, enough time might be required for the back diffusion of the substrate into the thrombin containing layer for inhibition of the thrombin to have taken place. Double layered strips were prepared to test this hypothesis. The bottom pad of the strip was Whatman 54 paper dipped in 5 mM aqueous S-2238 and dried at 35° C. for 30 minutes, and the upper pad was thrombin containing paper prepared by Method B using a dip solution which contained 2.0 NIH units/ml bovine thrombin and 0.2% BSA in 1.5M TRIS, pH 8. FIG. II graphically represents the response of this strip to plasma AT-III diluted in aqueous heparin. It can be seen that there is a definite response of the thrombin in the top pad to inhibition by the At-III in the sample. This indicates that the time necessary for the diffusion of the S-2238 substrate from the bottom pad to the upper pad containing the thrombin is long enough for the inhibitory thrombin.AT-III complex to form. The dose response shown in FIG. II could be useful to assay plasma containing 10–130% normal AT-III levels at a 60 fold dilution of plasma into aqueous heparin solution. A second experiment was performed using a strip containing twice as much thrombin in the top pad. FIG. III shows that a dose response is achieved which could be useful to assay plasma containing 10% to 130% normal AT-III levels at a 40 fold dilution of plasma into aqueous heparin solution. Both of these reagent strip preparations show an initial lag phase in the K/S vs. time curves (cf. FIG. IV) followed by a linear portion. This lag phase is no doubt the period in which the substrate, which must diffuse up from the bottom pad, has not reached saturation levels for the enzyme.

EXAMPLE III

A Fluorogenic Strip Responsive to Plasma AT-III Diluted in Aqueous Heparin

A double layered reagent strip containing the fluorogenic substrate phe-pro-arg-AIE was prepared as follows:

(1) Substrate containing paper was made by Method A using 5 mM D-phe-pro-arg-AIE in 0.1M Tris, 0.3M NaCl, pH 8.3 as a dip solution.

(2) Thrombin containing paper was prepared by Method B using a dip consisting of 1.5M tris-Cl, 0.2% BSA, 1.6 NIH units/ml.

(3) The reagent strips were prepared by Method 3 and tested by adding 60 µl of a plasma diluted in aqueous heparin and following the fluorescence generated on an SLM model 8000 spectrofluorometer modified to read strips in the horizontal position. FIG. V indicates that the response to plasma AT-III is similar to that of the chromogenic strips.

Example IV

A Chromogenic Strip Containing Heparin Responsive to Plasma AT-III Diluted In Water In the previous examples, plasma was diluted into solutions containing heparin. In this example, the feasibility of incorporating heparin directly into the strip was tested. A double layered reagent strip containing the chromogenic substrate S-2238 was prepared as follows:

(1) Substrate containing paper was made by Method A using 5 mM S-2238 in water as a dip solution.

(2) Thrombin containing paper which also contained heparin was made by Method B using the following dip solutions: Strip Preparation III-1.5M tris-Cl, 0.2% BSA, 10 USP units/ml heparin and 5.3 NIH units/ml bovine thrombin. Strip Preparation IV was the same as III except that the heparin concentration was 30 USP units/ml. The reagent strip laminates were prepared by Method 2. FIG. VI shows the rsponse of reagent Strip Preparation III and FIG. VII shows the response of reagent Strip Preparation IV to aqueous dilutions of plasma AT-III. Although the dose response is similar to that for plasma AT-III diluted in heparin solutions, the slopes of the d (K/S)/dt vs. plasma AT-III curves are less steep.

EXAMPLE V

A chromogen reagent strip prepared as described in Example II is used with 2 or more calibrator solutions which contain known amounts of AT-III in a matrix similar to blood plasma. Each calibrator is diluted 40 fold in an aqueous solution containing 3 USP units/ml of heparin. Thirty microliter aliquots of the diluted calibrators are applied to the reagent strips and the reflectance of each reagent pad monitored at 405 nm for 3 minutes subsequent to sample application. The slopes, d(K/S)/dt, of these kinetic curves are calculated by linear regression using the data collected between 90 seconds and 180 seconds. The slopes of the calibrators are plotted verses their known AT-III concentrations to create the calibration or standard curve plot which will be used to determine the AT-III concentrations of plasma samples.

After the calibration curve is prepared, the plasma or serum samples, for which assays of the AT-III concentration are desired, are diluted 40 fold in an aqueous solution containing 3 USP units of heparin/ml. Thirty microliter aliquots of each diluted plasma or serum sample are applied to reagent strips and their reflectance monitored at 405 nm every 5 seconds for 3 minutes. The slope, $d(K/S)/dt$, of this kinetic curve is calculated by a linear regression analysis from the data between 90 and 180 seconds. This slope value is located on the calibration curve and the AT-III concentration read from the opposite axis.

What is claimed is:

1. A method for the quantitative determination of AT-III in mammalian blood plasma which comprises:
    (a) contacting the plasma with excess heparin and a 3 layered reagent strip comprising:
        i. a first layer of a carrier matrix containing excess thrombin and a buffer;
        ii. a second lower layer adjacent to and in liquid communication with the first layer said second layer comprising a carrier matrix containing a thrombin sensitive fluorogenic or chromogenic substrate and a buffer, said substrate being capable of interacting with thrombin in such a manner that a time related chemical change detectable by fluorometric or spectrophotometric means takes place when thrombin and the substrate are contacted in a suitable liquid environment, wherein the material of the first layer is capable of adsorbing the plasma and allowing a portion of it to flow through into the lower layer which lower layer is of a material which allows the plasma fluid to solubilize the substrate and permits it to diffuse from the lower layer to the first layer after the AT-III in the plasma and the thrombin in the first layer have formed a thrombin AT-III complex; and
        iii. a layer of water impermeable material beneath the lower layer;
    (b) monitoring any chemical change in the substrate by reflectance spectrofluorometric or reflectance spectrophotometric means repeatedly over a period of time to obtain at least 2 fluorometric or spectrophotometric values as a function of time; and
    (c) comparing the relationship between the values obtained in step (b) with values obtained in a like manner using plasma samples containing known amounts of antithrombin-III and using such comparison to determine the concentration of antithrombin-III in the plasma sample being tested.

2. The method of claim 1 wherein the first and second layers are made of filter paper.

3. The method of claim 1 wherein the thrombin sensitive material is the chromogenic substrate H-D-phe-pip-arg-pNA.

4. The method of claim 3 wherein the buffer is capable of maintaining a pH of 8.0 to 8.5.

5. The method of claim 1 wherein the thrombin sensitive material is the fluorogenic substrate D-phe-pro-arg-AIE.

6. A test device suitable for the quantitative determination of AT-III in mammalian blood plasma which comprises:
    i. a first upper layer of a carrier matrix containing excess thrombin and a buffer;
    ii. a second layer adjacent to and in liquid communication with the first layer said second layer comprising a carrier matrix containing a thrombin sensitive fluorogenic or chromogenic substrate and a buffer said substrate being capable of interacting with thrombin in such a manner that a time related chemical change detectable by fluorometric or spectromphotometric means takes place when thrombin and the substrate are contacted in a suitable liquid environment, said device being further defined in that the material of the first layer is capable of absorbing the plasma and allowing a portion of it to flow through into the second layer which second layer is of a material which allows the plasma fluid to solubilize the substrate and permits it to diffuse from the second layer to the first layer after the AT-III in the plasma and the thrombin in the first layer have formed a thrombin-At-III complex; and
    iii. a third layer of water impermeable material beneath the second layer.

7. The device of claim 6 wherein the first and second layers are made of filter paper.

8. The device of claim 6 wherein the thrombin sensitive material is the chromogenic substrate H-D-phe-pip-arg-pNA 9. The device of claim 8 wherein the buffer is capable of maintaining a pH of 8.0 to 8.5.

10. The device of claim 6 wherein the thrombin sensitive material is the fluorogenic substrate D-phe-pro-arg-AIE.

* * * * *